United States Patent [19]
Park et al.

[11] Patent Number: 5,654,258
[45] Date of Patent: Aug. 5, 1997

[54] HERBICIDAL COMPOSITION COMPRISING TRIFLURALIN IN A POROUS CARRIER

[75] Inventors: Darren James Park; Gottfried Lichti, both of Victoria, Australia

[73] Assignee: Daratech Pty. Ltd., Melbourne, Australia

[21] Appl. No.: 525,707

[22] PCT Filed: Mar. 17, 1994

[86] PCT No.: PCT/AU94/00137

§ 371 Date: Sep. 13, 1995

§ 102(e) Date: Sep. 13, 1995

[87] PCT Pub. No.: WO94/21121

PCT Pub. Date: Sep. 29, 1994

[30] Foreign Application Priority Data

Mar. 19, 1993 [AU] Australia .............. PL7920/93

[51] Int. Cl.[6] .............. A01N 33/18; A01N 25/08; A01N 25/22
[52] U.S. Cl. .............. 504/347; 71/DIG. 1
[58] Field of Search .............. 504/347, 116; 71/DIG. 1

[56] References Cited

U.S. PATENT DOCUMENTS

| | | | |
|---|---|---|---|
| 4,174,960 | 11/1979 | Hendriksen | 71/121 |
| 5,073,191 | 12/1991 | Misselbrook et al. | 71/121 |
| 5,296,450 | 3/1994 | Kimler et al. | 504/116 |

FOREIGN PATENT DOCUMENTS

| | | |
|---|---|---|
| 0380325A2 | 1/1990 | European Pat. Off. . |
| 2137095 | 3/1984 | United Kingdom . |

OTHER PUBLICATIONS

IL, A, 84–219 (Ben–Gurion Univ. of Negev.) "Herbicidal Composition Comprising Alachlor or Trifluralin Microcapsules Formed from Reaction Prod. of Toluylene Diisocyanate and Polyfunctional Amine," Oct. 10, 1991 (abstract).

*Primary Examiner*—S. Mark Clardy
*Attorney, Agent, or Firm*—Walter H. Dreger; Jan P. Brunelle

[57] ABSTRACT

A solid, water dispersible, storage-stable trifluralin formulation comprises trifluralin supported inside porous, finely divided carrier particles, optionally together with at least one compatible wetting agent and/or dispersant additive, wherein the trifluralin is in the orange polymorphic form and the particles of the formulation are size-stable.

38 Claims, 6 Drawing Sheets

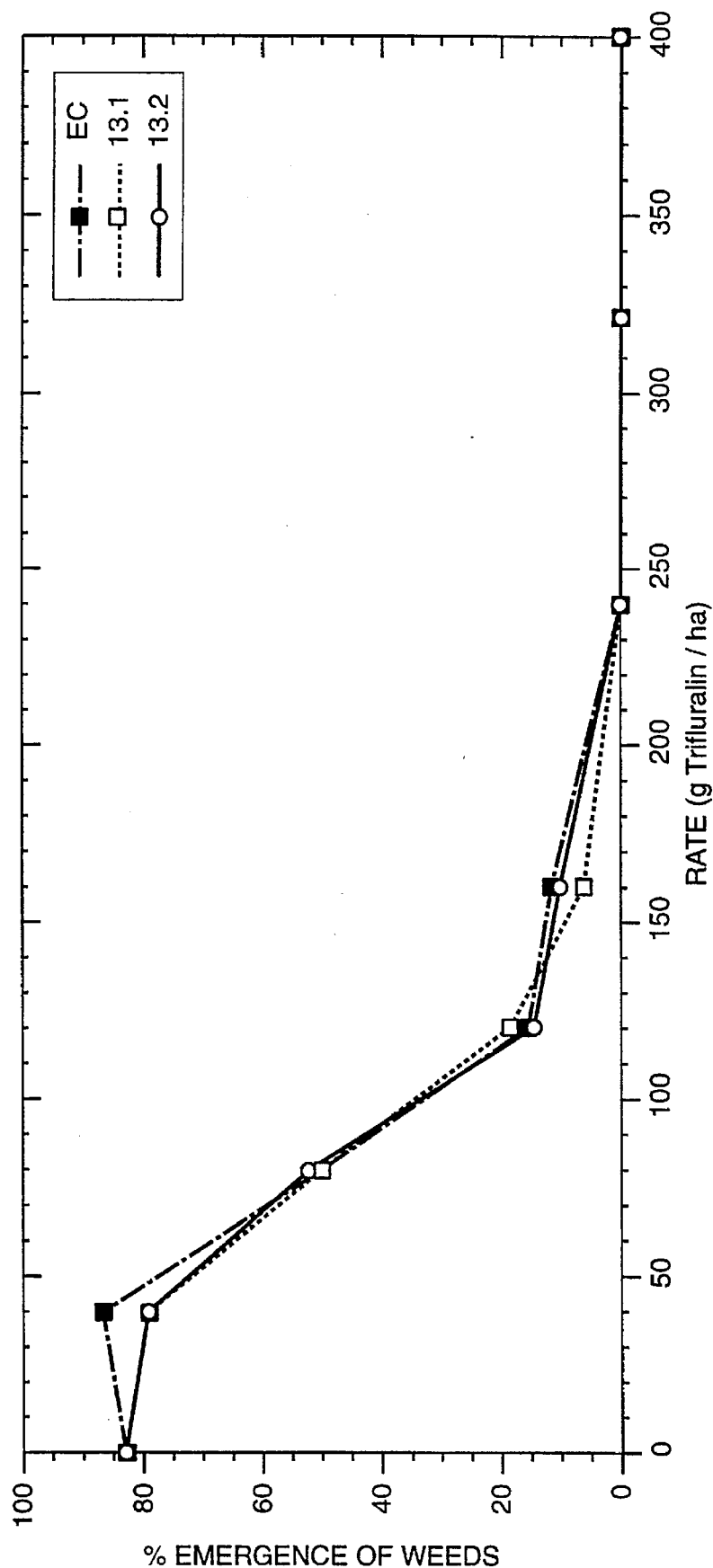
FIG._1

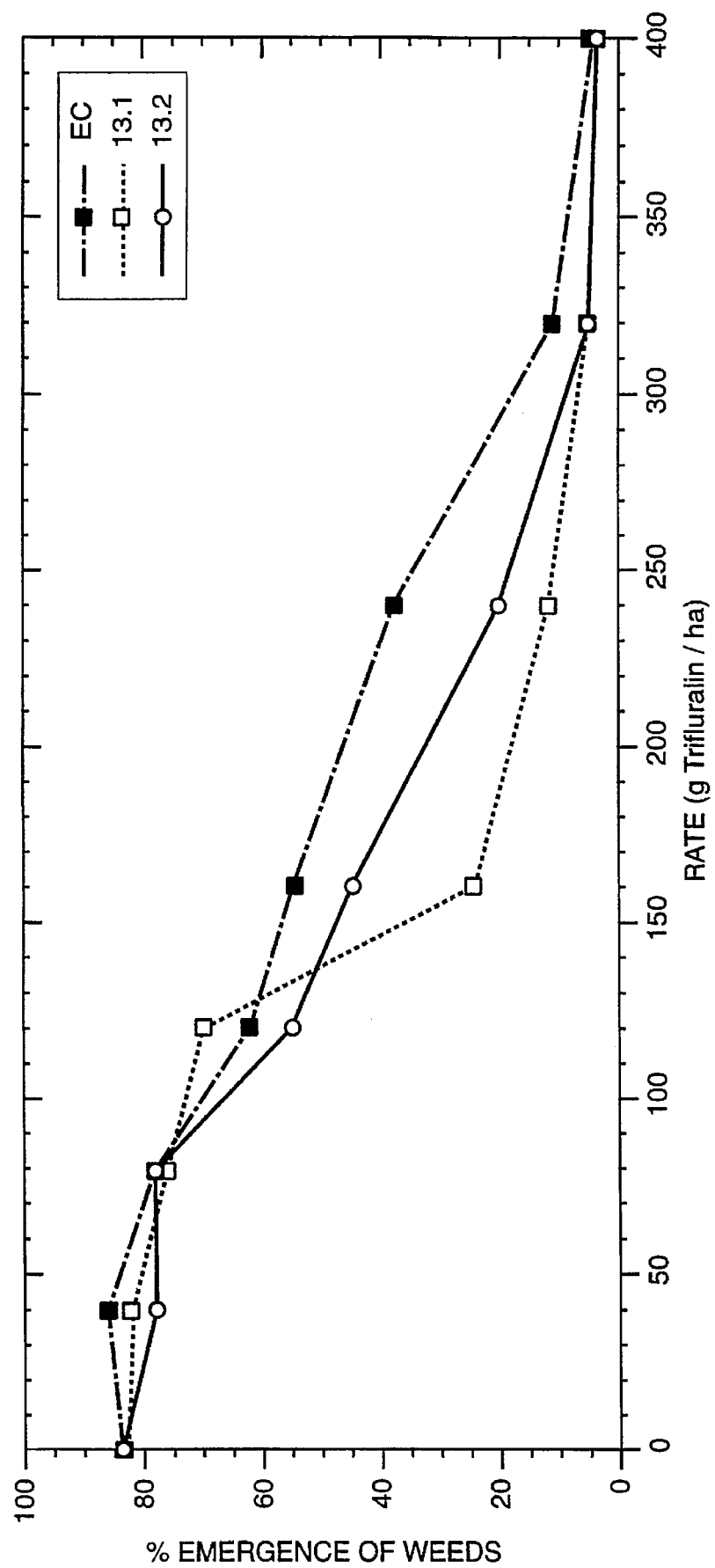
FIG._2

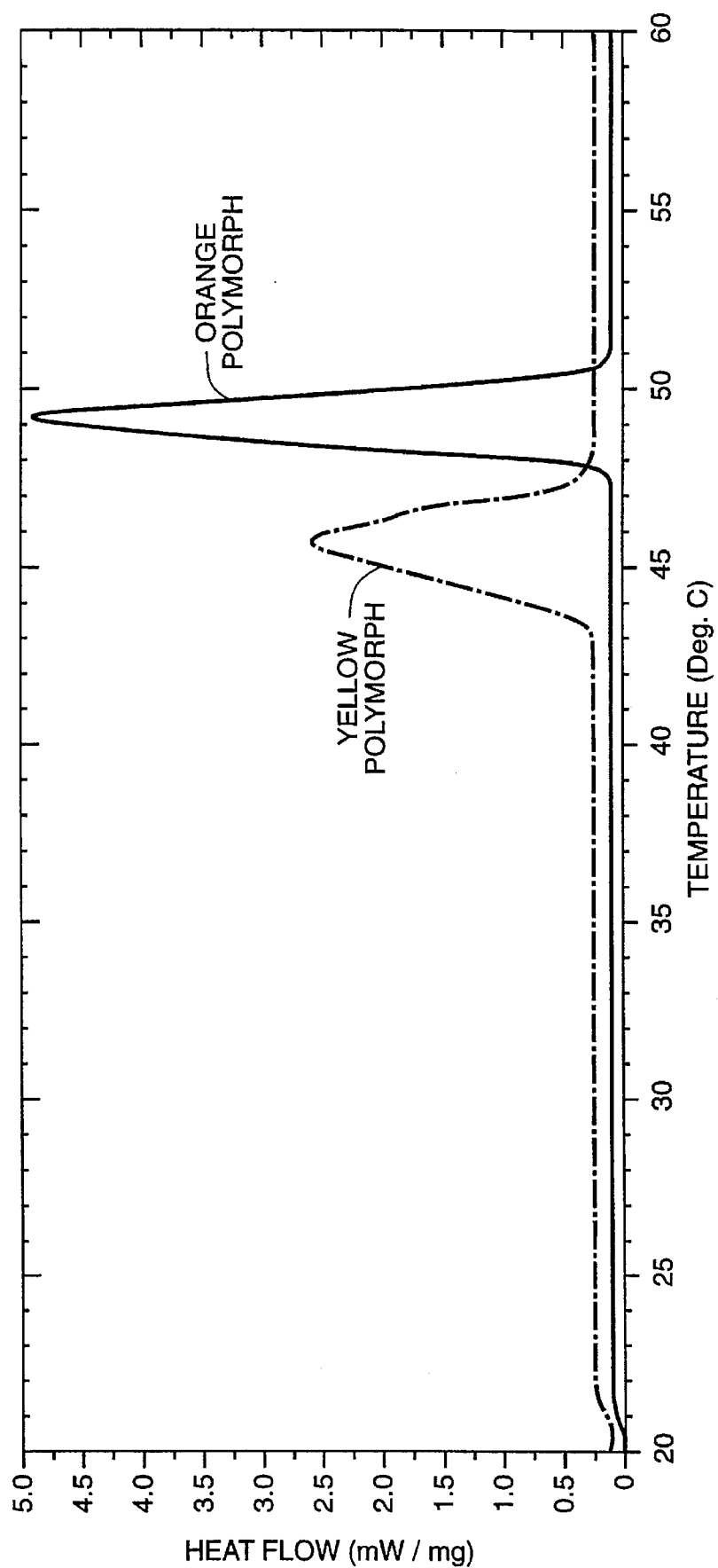

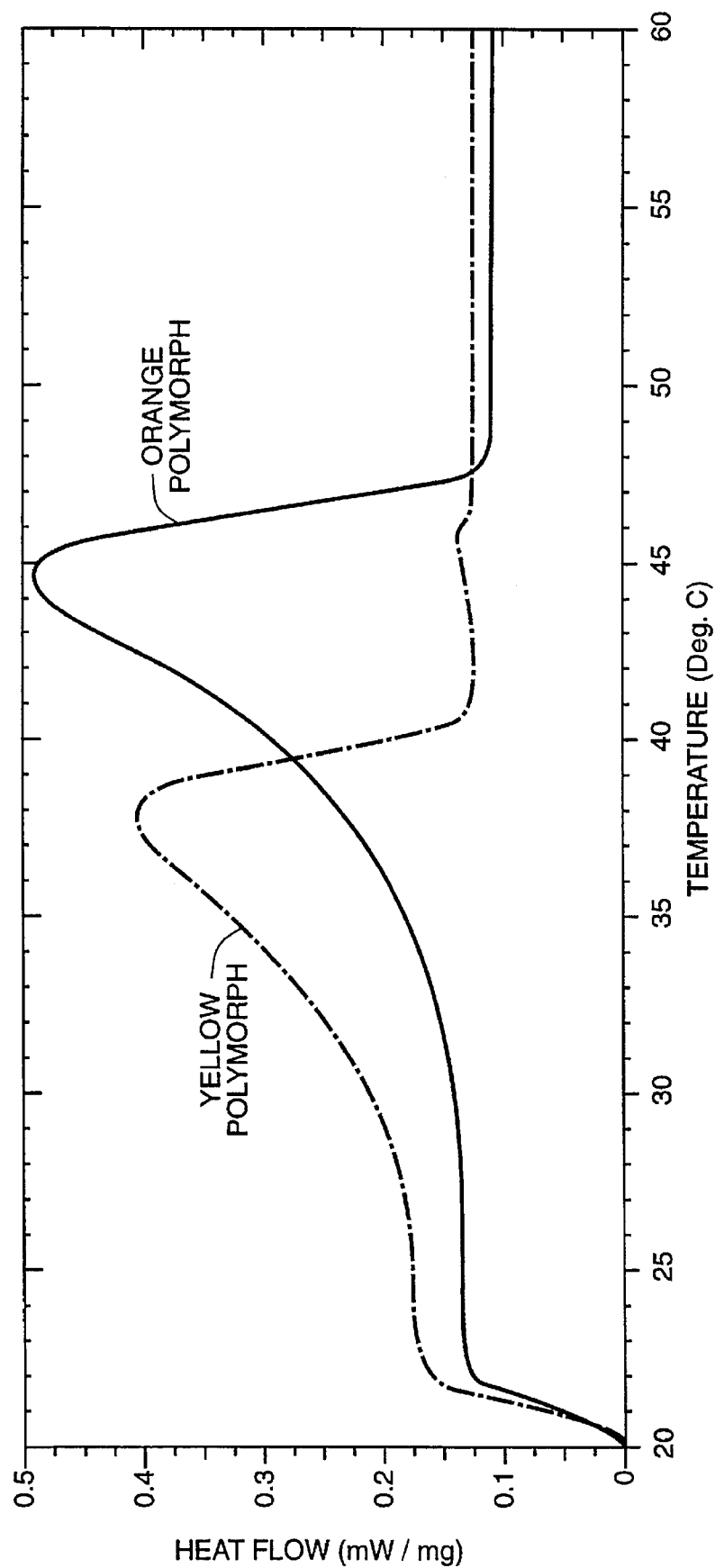
FIG._4

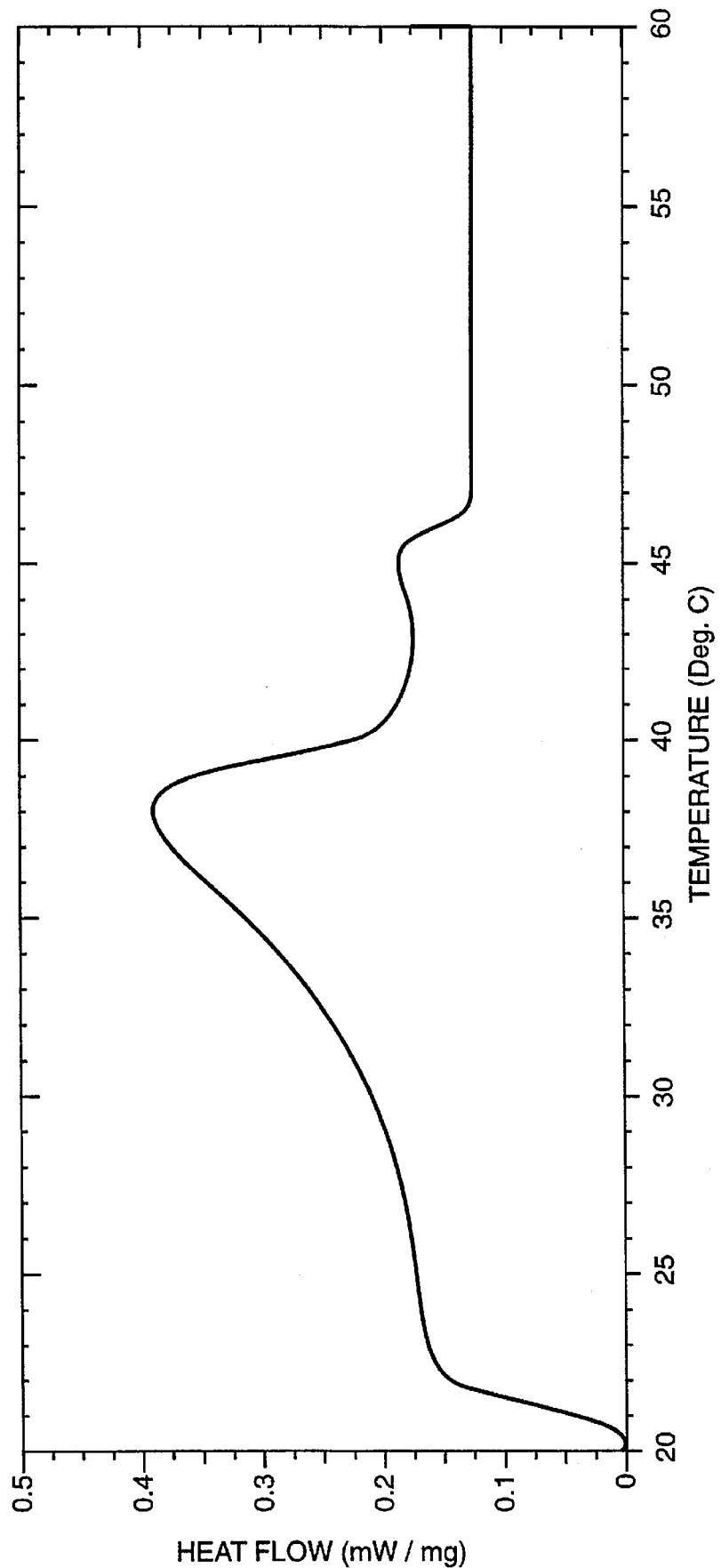
FIG._5

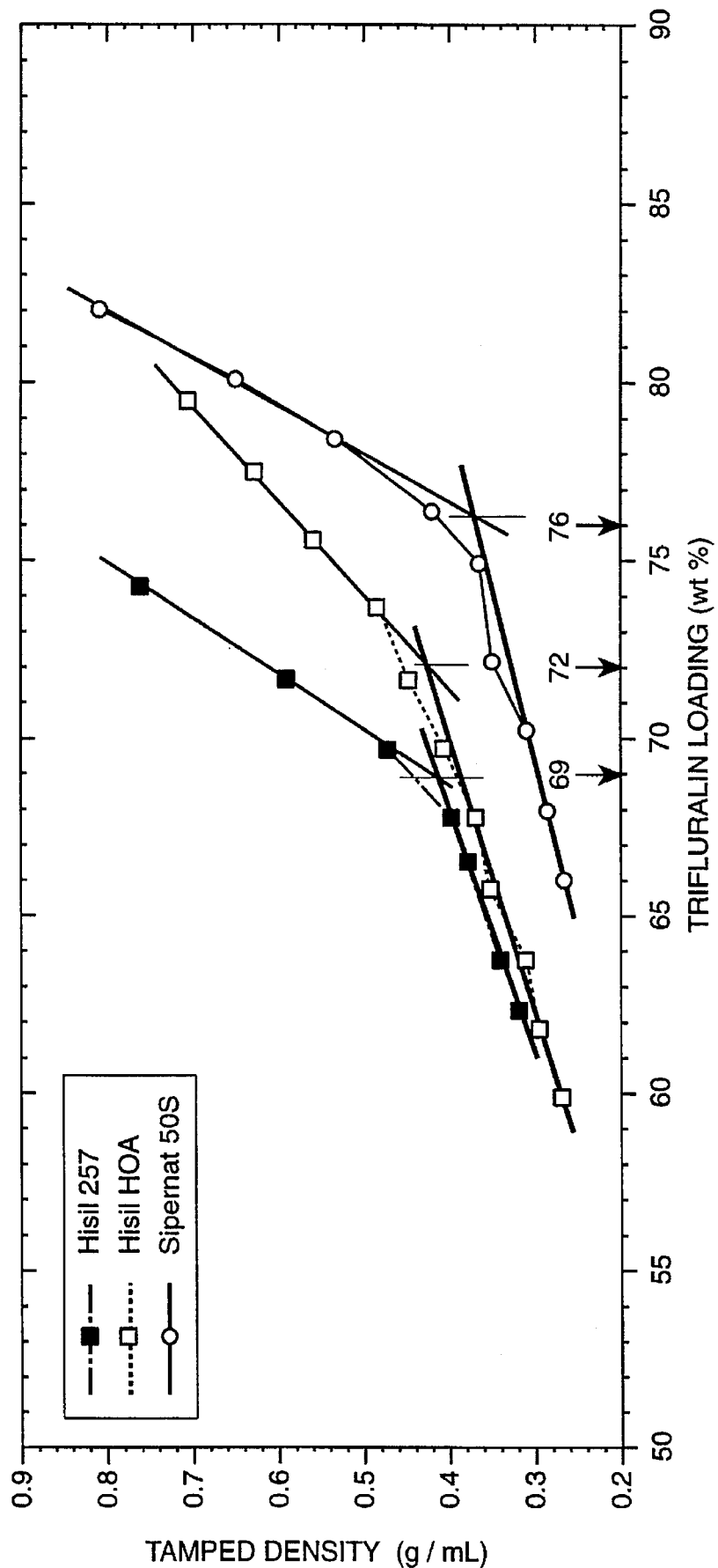
FIG._6

HERBICIDAL COMPOSITION COMPRISING TRIFLURALIN IN A POROUS CARRIER

This application has been filed under 35 USC 371 as a national stage application of international application PCT/AU94/00137 filed Mar. 17, 1994.

FIELD OF THE INVENTION

This invention relates to storage-stable formulations of trifluralin, in particular solid water-dispersible formulations, and methods for the preparation thereof.

BACKGROUND OF THE INVENTION

Trifluralin ($\alpha,\alpha,\alpha$-trifluoro-2,6-dinitro-N,N-dipropyl-p-toluidine) is a pre-emergent herbicide with little post-emergent activity. Formulations of the herbicide trifluralin are typically added to spray water at the point of use, and are applied as a fine spray to soil for the purpose of controlling undesirable weeds.

Conventionally, trifluralin formulations for use as aqueous sprays are emulsifiable concentrates. These formulations are liquids which contain a significant quantity of hydrocarbon solvent. Problems may arise from flammability, solvent contamination of the environment, and in the requirement for rigid solvent resistant storage containers which require elaborate disposal strategies.

Solid water-dispersible trifluralin formulations have been proposed, however the main problem associated with the use of solid water-dispersible trifluralin formulations is the problem of long term storage stability. Under prolonged storage, the formulations may be routinely subject to temperatures in the range 0° to 40° C. and may occasionally be subject to temperatures in the ranges −20° to 0° C. and 40° to 55° C. Under such storage conditions, some large (greater than 125 micron) particulate entities may form. These large particulate entities, which may account for less than 3% of the total formulation, fail to redisperse into fine particles (sub 125 micron) in the spray water, and cause blockages in the filters and nozzles of the spraying equipment. In commercial practice, such filters may have a mesh size of as little as 150 microns and it is desirable that a safety margin of at least 25 microns is achieved between the mesh size of the filter and the maximum particle size in the formulation. Filter blockages in the spraying equipment can lead to unacceptable delays in practical usage (such as down-time of major spray rigs), and even to loss in biological efficacy arising from departures from the desired rate of application. It is believed that one cause of the formation of large particulate entities may be coalescence which occurs when the trifluralin melts and freezes.

Currently available tests of long-term storage stability of trifluralin formulations are time consuming and it is frequently difficult to emulate practical storage conditions in laboratory storage tests. There is therefore a dual need. The primary need is to produce trifluralin formulations that do not fail in the field, and the secondary need is to find reliable and simple short-term tests for testing the long-term stability of these formulations.

Australian Patent No. 639678 (corresponding to U.S. application Ser. No. 301458, dated 24 Jan. 1989) discloses that solid trifluralin exists in yellow and orange polymorphic forms. The specification of this patent states that the yellow polymorph of trifluralin has higher herbicidal activity, better water dispersibility and enhanced storage stability compared to the orange polymorph of trifluralin. This specification also describes a method for producing a solid formulation comprising substantially yellow polymorph, the method involving the formation of a molten trifluralin-in-water emulsion in the presence of a water-soluble film-forming polymer such as polyvinyl alcohol-acetate. The emulsion is spray-dried to form dry product, and the yellow polymorph is stabilised by the use of crystallisation initiators such as sodium benzoate, and by the use of crystal stabilisers, such as sodium dioctyl sulfosuccinate. The thermal regime to which the newly manufactured material is subjected is stated to be critical. In particular, it is noted that rapid cooling which results in cold (−5° to 5° C.) powder is an efficacious method for stabilising the yellow form.

The yellow trifluralin powder made by the above process performs well in accelerated storage trials which involve heating and cooling of the formulation through the melting point of trifluralin. However, in long-term storage tests, for example, 6–12 months at ambient temperatures, it has been found that there is a gradual deterioration over time and a small quantity of orange polymorph crystals form in the formulation. This may be sufficient to block filters and nozzles in spray equipment.

In addition to the yellow and orange polymorphic forms previously mentioned, a third, amorphous (super-cooled) form of trifluralin is also known. When trifluralin is prepared in powder form it is possible (but not necessary) that trifluralin powder particles of yellow crystalline, orange crystalline, and amorphous polymorphic type co-exist in the formulation. Generally, individual powder particles are all amorphous or all yellow crystalline or all orange crystalline. Very infrequently mixed yellow crystal-orange crystal particles may be detected by microscopy. Mixed crystal-amorphous particles exist only for brief periods of time.

In a given powder sample in which different polymorphic forms of trifluralin co-exist, individual amorphous powder particles are generally randomly distributed throughout the sample. However, the situation for crystalline particles is quite different. Particles of a particular crystalline polymorphic type (yellow or orange) will generally be found in discrete macroscopic regions throughout the powder samples. For example, a substantially orange powder may have distinct yellow regions in it, and a substantially yellow powder may have distinct orange regions in it. The diameter of these regions is usually 1 mm or more and more usually 2 mm or more. The interior of the individual regions is quite homogeneous although mixed-crystal areas evidently occur along the boundaries of the regions.

Because of the colour-masking effects of various formulation additives, it is difficult to visually assess whether a particular uniform powder exists in yellow, orange or amorphous forms. However, uniform amorphous powders are easily characterised using crossed-polaroid light microscopy, and uniform crystalline powders are easily characterised by differential scanning calorimetry (DSC).

In mixed polymorphic powders, the amorphous content can be established by crossed-polaroid light microscopy and the co-existence of macroscopic yellow/orange regions is clearly apparent on visual inspection by the existence of regions or striations of a particular colour against a different coloured background. The actual colour is influenced by formulation additives.

SUMMARY OF THE INVENTION

It is an object of the present invention to provide a solid, water-dispersible, storage-stable trifluralin which overcomes or alleviates one or more of the problems associated with the prior art formulations.

According to the present invention there is provided a solid water-dispersible, storage-stable trifluralin formulation comprising trifluralin supported inside porous, finely divided carrier particles, said trifluralin being orange-stable (as defined herein) and the particles of said formulation being size-stable (as defined herein).

In particular, it has been found that orange polymorph trifluralin can be loaded into porous particles at a level not exceeding 98% of the pore volume capacity of the particles, and preferably not exceeding 95% of the pore volume capacity, and more preferably not exceeding 90% of the pore volume capacity, to produce a formulation that meets the criteria of orange-stability and size-stability as set out below.

Furthermore, it has been found that the formulations of this invention have bioefficacy equivalent to or better than commercially available liquid formulations of trifluralin (that is, emulsifiable concentrates).

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

In view of the teaching of Australian Patent No. 639678 concerning the superiority of yellow polymorph trifluralin for storage purposes, the present inventors made the surprising discovery that powder samples which meet both the orange-stable and the size-stable criteria set out below are more stable in long-term storage than those which do not. It has surprisingly been found that trifluralin formulations which are storage stable over the long term can be made by absorbing trifluralin inside highly porous, finely divided carrier particles in such a way that the formulation has both short-term orange stability and short-term size stability.

The following thermal challenge test is used to establish the criteria of orange-stability and size-stability in accordance with this invention.

In the thermal challenge test, 12 g of powder sample in a 50 ml container is heated from 25° to 55° C. over 6 hours (uniform rate of heating, provided by a temperature-programmable oven). Sample is held at 55° C. for 6 hours and then cooled (uniform rate of cooling) to 25° C. over 6 hours. Temperature is kept at 25° C. for 6 hours.

The following protocol is used to determine the upper limit of particle size distribution to establish whether or not the particle size of a formulation exceeds 125 µm. 5 g of powder is added to 300 mls of water under rapid magnetic stirring for two minutes. The resulting dispersion is poured through a 125 µm sieve of diameter 3 cm. The residue on the sieve is compared with standard sieve residues of various amounts. If less than 0.005 g of residue is found on the sieve, the sample is considered to have not exceeded 125 µm.

The term "orange-stable" when used herein means that in a given formulation sample, both before and within 24 hours after the thermal challenge, more than 80% of the trifluralin is in orange polymorphic form and less than 15% of trifluralin is in amorphous form, and any local regions in the sample which contain substantially yellow polymorphic trifluralin have diameters of 2 mm or less, preferably 1 mm or less, and more preferably cannot be detected.

The existence in the sample of local regions which contain substantially yellow polymorphic trifluralin can be ascertained by:

(a) visual inspection of the powder at the surface of the sample, and
(b) formation of a new surface, for example by removal of powder at the pre-existing surface, followed by visual inspection of the powder at the newly-formed surface.

Preferably, in an "orange-stable" formulation sample, more than 90% (and more preferably more than 95%) of the trifluralin is an orange polymorphic form and less than 5% (and more preferably less than 1%) of the trifluralin is in amorphous form, both before and after the thermal challenge test, with the balance, if any, in yellow polymorphic form in local regions which have diameters of 2 mm or less.

The term "size-stable" when used herein means that in a given formulation sample, the particle size does not exceed 125 µm, both before and within 24 hours after the application of the thermal challenge test as described above. Preferably, the particle size of the formulation does not exceed 70 µm, more particularly 50 µm, both before and after the thermal challenge test. Particularly preferred formulations in accordance with this invention are "size-stable" formulations in which 80% of particles are within the range 5-30 µm.

Trifluralin meeting the "orange-stable" criterion of this invention should be of a purity of 93-99 wt % preferably at least 97 wt %.

Preferably, the formulation of this invention also comprises at least one compatible wetting agent and/or dispersant additive to facilitate the dispersion of particles in spray water at the point of use.

A compatible additive is an additive which when added to a formulation in accordance with the present invention does not result in the formulation failing to meet the "orange-stable" and "size-stable" criteria defined herein. The compatibility of an additive such as a surfactant may be readily tested by adding the additive to the Reference Formulation (described in Example 2 hereinafter) and determining whether the resultant formulation meets both the "orange-stable" and "size-stable" criteria.

The dispersant and/or wetting agent may be chosen from any of the materials or blends of materials commonly used to disperse solid particles in water, providing that the previously mentioned compatibility requirement is satisfied. However, it has been found that consistently good results are given by taurine-type dispersion agents, for example the sodium salt of N-methyl-N-oleoyltaurate, which is available commercially under the trade name HOSTAPON T, (manufactured by Hoechst). In addition, the wetting agent alkyl napthalene sulfonate sodium salt may also be added, which is available commercially under the trade name MORWET EFW (Witco, Dallas, USA). Typically, a dispersant may be added in an amount of 2 to 10 wt %, preferably 3 to 6 wt % of the final product, and a wetting agent in an amount of 0.5 to 5 wt %, preferably 1 to 3 wt % of the final product.

It has been proposed to facilitate the dispersibility of particulate solids in water by incorporating with them a small proportion, typically 5-10% by weight, of a pulverised clay such as, for example, kaolin or attapulgite. Such aids to dispersibility are relevant to the present formulations also.

The formulated powders of the present invention may, if desired, be blended with other particulate formulations comprising other compatible active ingredients, in particular other herbicides.

Any suitable porous, finely divided particles may be used as carrier particles in accordance with this invention. The porous particles are preferably finely divided porous inorganic particles having a surface area of at least 60 m²/g. Preferably, the finely divided porous particles consist of primary particles of amorphous silica or of silicates which have been formed by precipitation in water and agglomerated into clusters having a surface area of 100 to 300 m²/g, more preferably 150 to 250 m²/g. Such particles, however, must be such that the "orange-stable" and "size-stable" criteria are met. For example, it has been found that when anhydrous silica porous powder is used, these criteria may not be met. Suitable carrier particles may, however, be readily ascertained by simple testing. Particularly preferred carrier particles are silica particles having a carrier surface area of 150 to 250 m²/g, and having an adsorbed water content of 2 to 12 wt %, preferably 3 to 6 wt %, before loading of the trifluralin.

When trifluralin is loaded inside porous silica particles, it has been observed that the melting points of orange and yellow trifluralin polymorphic forms are reduced by 5°–10° C., and amorphous trifluralin may persist for extended periods of time. Furthermore, the colour of the trifluralin may be masked by the presence of the powder.

For a given sample containing trifluralin inside a porous carrier powder, the trifluralin can be converted to substantially pure yellow form by melting, followed by rapid chilling to −2° C. This procedure provides a basis for calibrating the DSC result: if the DSC result for a sample is the same both before and after melting/chilling, the original sample was substantially in the yellow form.

The existence of amorphous trifluralin in powder formulations may be established by dispersing the powder in water and examining the dispersion by light microscopy in cross-polarised or partially cross-polarised light. Under these conditions unloaded silica particles in water are virtually invisible whilst silica particles which contain crystalline (orange or yellow) trifluralin appear brightly coloured and sparkling. However, amorphous trifluralin-in-silica may be detected by the presence of dull, featureless slightly coloured silica particles. Particles at the lower end of the particle size distribution should not be used to establish the state of trifluralin by microscopy. The percentage amorphous trifluralin content in a given formulation can be obtained by counting the number of amorphous particles in a representative field of view under the microscope (cross-polarised or partially cross-polarised configuration) and dividing by the total number of particles. Only particles of size 10 microns or greater should be used in this determination.

The trifluralin should be present in the carrier particles in an amount such that there is no substantial deposit of trifluralin externally on the particles. It has been found that if the amount of the absorbed trifluralin exceeds about 98% of the pore volume of the carrier, trifluralin will coat the outer surface of some of the particles and cause agglomeration. Preferably, the volume of trifluralin does not exceed about 95% of the pore volume of the carrier, and more preferably does not exceed 90% of the pore volume of the carrier. The effective pore volume of a carrier may be inferred from the results of the oil absorption test (ASTM D2414), however a more useful method is described in Example 15 below. The latter method has been used to establish the preferred percentage of pore volume ranges in accordance with this invention.

For reasons of economy of application, it is desirable to have as high a weight proportion of active ingredient on carrier as is consistent with the above specification. Preferably, the trifluralin comprises from 50–70 wt %, more preferably from 55–65 w%, of the formulation.

The following protocol is used to establish the maximum amount of trifluralin which can be loaded into the pores of a carrier particle. This amount is expressed as a percentage weight of trifluralin on the total weight of the loaded powder.

A series of powder samples (each containing 3 g of unloaded carrier powder) are heated at 105° C. for 2 hours in an open glass container. Various amounts of molten trifluralin (80° C.) are added to the hot powders under stirring for two minutes. The samples are left to cool and crystallise at 15°–20° C. for 24 hours. Crystallisation into the orange form is encouraged by seeding the samples after 1 hour of cooling with a small amount of trifluralin Reference Formulation (Example 2). Each sample is then brushed through a 250 μm sieve and the tamped density is measured. This is graphed against percentage trifluralin loading. The curve of density vs loading is linear in two regions—one below the maximum loading level and one above. The point of extrapolated intersection of these two lines is noted. This point of intersection is taken to be the maximum trifluralin loading for the carrier (see Example 15).

The following protocol is used to check the long term stability of a trifluralin formulation and reflects the fact that commercially viable formulations must be stable after melting in storage.

The formulation is subjected to the thermal challenge test as previously described, and is then stored at ambient temperatures for 6–18 months and treated as in the prior protocol for testing the maximum size of particles in a formulation. The formulation is considered to have long-term stability if the maximum particle size at 6–18 months as determined by the prior protocol is less than 125 μm.

The biological efficacy of a powder formulation may be evaluated according to the following protocol.

Alkaline sandy loam soil as typical of the Mallee, Victoria, Australia is air dried and brought to a 10% level of water by weight. The soil is placed into containers of dimension 85 mm×140 mm×50 mm (depth) and the containers of soil are sprayed at rates of formulation in the range 0–1.5 liters/hectare of trifluralin emulsifiable concentrate. The reference commercially available emulsifiable concentrate formulation contains 40 % trifluralin active. A spray volume of 60 liters/hectare of water is used and the dilute formulations are sprayed through spraying system nozzles of type 11003 using 200 kilopascals of air pressure at ambient temperature 20°±3° C. After spraying, soil in the containers is treated in two ways:

(a) Immediate Incorporation: the soil is immediately mixed thoroughly to effect instant and complete incorporation of active ingredient, and is returned to the container.

(b) 48 Hour Incorporation: the soil is left for 48 hours after spraying and thereafter is mixed thoroughly and returned to the soil.

Soil portions as treated as in (a) or (b) above are sown at 24 hours after mixing with 20 seeds of annual ryegrass (Lollium rigidum) to a depth of 1 cm. The samples are kept at 18°–22° C. in a glasshouse for 10 days and are watered twice daily. The results are obtained by calculating the percentage emergence of ryegrass from each container of soil at 10 days.

The present invention also provides a method for the preparation of the formulation of the present invention which comprises the steps of adding molten trifluralin to heated carrier particles, maintaining the mixture at a temperature above the melting point of trifluralin for a period of time sufficient to allow substantially all of the trifluralin to be absorbed by the carrier particles, and then gradually cooling the carrier particles to a temperature in the range of 15° to 25° C. over a time period of ½ to 12 hours.

In this method, the trifluralin may be introduced into the pores of the finely divided porous carrier in molten form by addition of molten fluid to the hot powder with stirring. The mixture is then maintained at a temperature above the melting point of trifluralin for a period of time sufficient to permit substantially all the trifluralin to be introduced into the pores. The mixture is then gradually cooled to room temperature. To obtain "orange-stable" and "size-stable" trifluralin as defined, the rate and degree of cooling must be carefully controlled. Both excessively rapid and excessively slow cooling and particularly cooling to temperatures outside the range 10°–25° C. must be avoided. Preferably, the mixture is introduced into a cooling zone at 15°–20° C., and then cooled in this zone under conditions such that the mixture is gradually cooled to a final temperature in the range of 15°–25° C., more preferably 15°–20° C. A desirable time for cooling to occur is between half an hour and twelve hours, preferably in practice between one and six hours. As a consequence of the carrier loading process, a degree of particle agglomeration may occur and it may be necessary to break up such agglomerated particles by a suitable process such as the process of hammermilling.

In yet another embodiment, the present invention provides a method for treating soil to prevent emergence of weeds thereon, which comprises:

forming an aqueous dispersion of a water-dispersible trifluralin formulation as broadly described above; and applying a herbicidally effective amount of said aqueous dispersion to the soil.

Further details of the present invention will be apparent from the following Examples which are included by way of illustration, not limitation, of the invention.

In the accompanying drawings:

FIGS. 1 and 2 are graphs showing the herbicidal activity of trifluralin formulations of the present invention when compared with commercially available emulsifiable concentrate (E.C.) trifluralin formulation, evaluated after immediate incorporation of the herbicide into soil (FIG. 1) and when incorporated 48 hours after spraying (FIG. 2);

FIGS. 3, 4 and 5 are DSC thermograms for pure trifluralin, trifluralin Reference Formulation according to this invention, and trifluralin mixed polymorphs, respectively; and FIG. 6 is a graph showing maximum trifluralin loading capacity of various porous carrier materials.

EXAMPLES

Example 1

This example illustrates the undesirable long-term storage behaviour of prior art yellow water-dispersible trifluralin powder formulations.

A yellow water-dispersible formulation of trifluralin was purchased from Dow-Elanco, USA. Upon receipt of the powder, it was immediately assessed for short-term orange stability and short-term size stability and was also assessed for long-term storage stability. The protocols for these assessments have been described above.

Performance Evaluation:

The powder passed the short-term size stability test but clearly failed the short-term orange stability test as it was substantially yellow. On standing for six months, local orange regions were observed to have formed in the powder and the powder failed the long-term storage stability test.

The aged powder was added to the tank of a spray rig and sprayed through a spraying system using nozzles of type 11003 at 200 kPa air pressure at an ambient temperature of 18°–22° C. The nozzles were observed to become blocked within five minutes of operation.

Example 2

This example illustrates the preparation and evaluation of a water-dispersible trifluralin powder formulation in accordance with the present invention. This formulation is designated as the Reference Formulation and will be compared with other formulations in later examples.

a. Materials:

1: Technical trifluralin herbicide (97% purity), supplied by Nufarm Australia.

2: H151L 257, a synthetic precipitated silica of surface area 190–210 sq.m/g manufactured by PPG (Taiwan), supplied by Abel, Lemon and Bleakely, Footscray, Melbourne, Australia.

3: HOSTAPON T, the trade name for dispersing agent (sodium-N-methyl-N-oleotaurate) manufactured by Hoechst.

4: MORWET EFW, the trade name for wetting agent (sulphated alkyl carboxylate and sulphonated alkyl naphthalene sodium salt) manufactured by Witco, Dallas, USA.

b. Composition of the Reference Formulation:

| | |
|---|---|
| Technical trifluralin, (97% pure) | 56.4 wt % |
| HISIL 257 silica | 35.7 |
| Adsorbed water | 1.9 |
| HOSTAPON T dispersant | 4.0 |
| MORWET EFW wetter | 2.0 |

The above formulation was 60 wt % of technical trifluralin on carrier particles (calculated as weight of trifluralin/total weight of trifluralin plus H151L 257 plus adsorbed water). This corresponds to 87% of the maximum loading level of trifluralin in the carrier particles (for H151L 257) as determined in Example 15.

c. Method of Preparation:

Molten trifluralin (240 g, 97% purity) at 100° C. was slowly poured into H151L 257 (160 g, 5 wt % water content) also at 100° C. with stirring. The Hisil 257 was contained in an insulated 2 liter metal tin and stirred using a stirrer consisting of 4 horizontal metal bars mounted on a central shaft. The horizontal bars extended across ¾ of the diameter of the tin. The stirring speed during addition was 500 rpm and the addition time was 5 minutes. After the last of the trifluralin was added, stirring was continued for 2 minutes at 1000 rpm. HOSTAPON T (17 g) and MORWET EFW (8.5 g) were then added while stirring and the stirring continued at 1000 rpm for a further 2 minutes. The resulting powder was then transferred to a non-insulated 2 liter metal tin in a room at 15°–20° C., to which temperature the powder cooled in 5–6 hours.

The cooled and crystallised powder was hammer-milled in a Raymond Lab mill at 2910 rpm through a screen size of 1.6 mm, and then through a screen size of 0.58 mm to give the final product.

d. Performance Evaluation:

The Reference Formulation passed the short-term size stability and the short-term orange stability tests (previously described). The powder also passed the long-term storage stability test (previously described) after twelve months.

In addition, the powder was stored at −2° C. for a period of ten weeks and then subjected to the filter test referred to in the long-term storage stability test. The powder passed this test.

Example 3

This example illustrates the use of a different method of preparation of a water-dispersible trifluralin powder formulation in accordance with this invention.

a. Materials and Composition:

The materials and composition of this formulation were as per Example 2.

b. Method of Preparation:

The powder was prepared as per Example 2 with the exception that the HOSTAPON T and MORWET EFW were stirred into to the cold powder after the first hammermilling step, rather than into the hot powder after trifluralin addition. The resulting mixture was then hammer-milled in a Raymond Lab mill at 2910 rpm through a screen size of 0.58 min.

c. Performance Evaluation:

The powder passed the short-term size stability and the short-term orange stability tests (previously described). The powder also passed the long-term storage stability test (previously described) after twelve months.

In addition, the powder was stored at $-2°$ C. for a period of ten weeks and then subjected to the filter test referred to in the long-term storage stability test. The powder passed this test.

Example 4

This example illustrates the preparation and evaluation of a formulation in which the trifluralin is present in the yellow polymorphic form.

Materials and Composition:

The materials and composition of this formulation were as per Example 2.

b. Method of Preparation:

The powder was made by taking 12 g of Reference Formulation (made as per Example 2) in a transparent 50 ml container and heating it in an oven for 12 hours at a temperature of 55° C. Thereafter the powder was placed in a constant temperature environment of 5 ° C. and left to cool and crystallise for 8 hours. The colour of the powder was observed to be substantially yellow (presence of the yellow polymorph was confirmed by DSG).

c. Performance Evaluation:

The powder failed the short-term orange stability test as it was substantially yellow polymorph. The powder passed the short-term size stability test. However, it subsequently failed the long-term storage stability test.

Example 5

This example illustrates the preparation and evaluation of a trifluralin powder formulation in accordance with this invention, but wherein the weight % loading of trifluralin in the carrier powder is less than that of the Reference Formulation (80% of maximum loading capacity compared to 87%).

a. Materials and Composition:

The materials used in this formulation were as per Example 2 with the composition as below;

| Technical trifluralin, (97% pure) | 51.7 wt % |
|---|---|
| HISIL 257 silica | 40.2 |
| Adsorbed water | 2.1 |
| HOSTAPON T dispersant | 4.0 |
| MORWET EFW wetter | 2.0 | b. Method of Preparation:

The method of preparation was as per Example 2 with the exception that less trifluralin was added to the carrier (55 wt % loading instead of 60 wt % loading). This loading level corresponds to 80% of the maximum loading level for H151L 257 (see Example 15).

c. Performance Evaluation:

The powder passed the short-term size stability and the short-term orange stability tests (previously described). The powder also passed the long-term storage stability test (previously described).

Example 6

This example illustrates the preparation and evaluation of a formulation which is short-term orange stable but not short-term size stable.

a. Materials and Composition:

The materials used in this formulation were as per Example 2 with the composition as below;

| Technical trifluralin, (97% pure) | 62.0 wt % |
|---|---|
| HISIL 257 silica | 30.4 |
| Adsorbed water | 1.6 |
| HOSTAPON T dispersant | 4.0 |
| MORWET EFW wetter | 2.0 | b. Method of Preparation:

The method of preparation was as per Example 2 with the exception that more trifluralin was added to the carrier (66 wt % loading instead of 60 wt % loading). This loading level corresponds to 96% of the maximum loading level for H151L 257 (see Example 15).

c. Performance Evaluation:

The powder passed the short-term orange stability test but failed the short-term size stability test. The powder also failed the long-term stability test.

Note that Examples 4 and 6 demonstrate that a pass result in either the short-term size stability test or the short-term orange stability test in isolation is not sufficient to ensure the long-term stability of a formulation. Furthermore, Examples 2, 3 and 5 demonstrate that a pass result in both the short-term orange stability and short-term size stability tests is a useful indicator of long-term stability.

Example 7

This example illustrates the preparation and evaluation of a range of formulations containing 0, 3, 5 and 10 wt % of adsorbed water in the porous silica carrier powder before loading of the trifluralin. Formulations containing 3, 5, and 10 wt % of adsorbed water in the carrier before loading lie within the preferred range of this invention, whereas 0 wt % does not.

a. Materials and Composition:

The materials used in this formulation were as per Example 2. Powders 7.1, 7.2, 7.3, and 7.4 correspond to samples wherein the initial adsorbed water content of the silica carrier was 0, 3, 5 and 10 wt %. After loading of the molten trifluralin, the final adsorbed water content of the samples lay in the range 0–3 wt % and the compositions of the powders was as per Example 5, except that the appropriate value for the adsorbed water was 0, 1.3, 2.1 and 3 wt % respectively.

b. Method of Preparation:

A series of powders were prepared with varying adsorbed water content as per Example 5. Particular care was taken to monitor the carrier adsorbed water content before loading of the trifluralin. To produce a powder with no water present, the carrier H151L 257 was dried for 24 hours in an open metal tin at 105° C. A weight loss of 6.7 wt % was observed. The same weight loss was also observed for a small sample of H151L 257 dried for 24 hours at 105° C. To produce a powder containing 3 or 5 wt % adsorbed water (before loading of the trifluralin), the carrier H151L 257 was heated in a metal tin with the lid on loosely at 105° C. and the weight monitored until a weight loss corresponding to the excess water above 3 or 5 wt % adsorbed was observed. For a water content of 10 wt % (before loading of the trifluralin), extra water was sprayed into the carrier.

c. Performance Evaluation:

|  | 7.1 | 7.2 | 7.3 | 7.4 |
|---|---|---|---|---|
| Short-term Orange Stability | fail | pass | pass | pass |
| Short-term Size Stability | pass | pass | pass | pass |
| Long-term Stability | fail | pass | pass | pass |

As may be seen from these of results, the powder made using anhydrous carrier powder passed the short-term size stability test but failed the short-term orange stability test. This powder also failed the long-term stability test.

Example 8

This example illustrates the preparation and evaluation of a range of formulations wherein the trifluralin purity varies through the range 90, 93, 95, 97 wt %. Formulations containing 93, 95 and 97 wt % pure trifluralin fall within the preferred range of this invention, whereas 90 wt % lies outside.

a. Materials and Composition:

The materials used in this formulation were as per Example 2 with the compositions described in the table below (powders 8.1, 8.2, 8.3 and 8.4 correspond to 90, 93, 95 and 97% purity trifluralin);

|  | 8.1 | 8.2 | 8.3 | 8.4 |
|---|---|---|---|---|
| (Pure Trifluralin) | (50.8) | (52.5) | (53.7) | (54.8) |
| Technical Trifluralin | 56.5 | 56.5 | 56.5 | 56.5 |
| HISIL 257 | 35.7 | 35.7 | 35.7 | 35.7 |
| Adsorbed water | 1.8 | 1.8 | 1.8 | 1.8 |
| HOSTAPON T | 4 | 4 | 4 | 4 |
| MORWET EFW | 2 | 2 | 2 | 2 | b. Method of Preparation:

Trifluralin technical (96–98% purity) was obtained in 20 kg pails. These were melted at 55° C. in an oven, stirred to homogenise and decanted into two liter cans. During crystallisation, an oily impurity separated which was collected. This material consisted of approximately 50% trifluralin and 50% various reaction byproducts. The oil thus collected was added back to technical trifluralin in order to adjust the purity using the normal spectrum of impurities which may be present in production samples. A series of powders were then made as per Example 2 using trifluralin of adjusted purity 90, 93, 95 and 97 wt % active ingredient.

c. Performance Evaluation:

|  | 8.1 | 8.2 | 8.3 | 8.4 |
|---|---|---|---|---|
| Short-term Orange Stability | fail | pass | pass | pass |
| Short-term Size Stability | fail | pass | pass | pass |
| Long-term Stability | fail | pass | pass | pass |

The formulation containing trifluralin of only 90 wt % purity was observed to have an elevated amorphous content (20%) and left significant residue in the filter test. This formulation also failed all tests.

Example 9

This example illustrates the preparation and evaluation of a range of formulations wherein the internal surface area of the silica carrier was varied in the range 200–450 sq.m/g and wherein the wt % loading of trifluralin in the carrier powder was varied in the range 87, 90 and 95% of the experimentally determined maximum loading level (described in Example 15).

a. Materials and Composition:

The materials used in this formulation were as per Example 2 and in addition two new carriers H151L HOA and SIPERNAT 50S were used as follows:

1: H151L HOA, a synthetic precipitated silica of surface area 155 sq.m/g manufactured by PPG (Taiwan), supplied by Abel, Lemon and Bleakely, Melbourne, Australia.

2: SIPERNAT 50S, the trade name for a synthetic precipitated silica of surface area 450 sq.m/g manufactured by Degussa, supplied by Degussa, Australia.

The powder compositions (wt %) are tabled below (powders 9.1, 9.2 and 9.3 correspond to H151L 257 loaded to 80, 87 and 95% of maximum loading, powders 9.4, 9.5 and 9.6 correspond to H151L HOA loaded to 80, 87 and 95% of maximum loading while powders 9.7, 9.8 and 9.9 correspond to SIPERNAT 50S loaded to 80, 87 and 95% of maximum loading);

| Carrier HISIL 257 | 9.1 | 9.2 | 9.3 |
|---|---|---|---|
| (Carrier Loading, wt % | 55 | 60 | 66) |
| Technical Trifluralin | 51.8 | 56.5 | 62.1 |
| HISIL 257 | 40.2 | 35.7 | 30.3 |
| Adsorbed water | 2.0 | 1.8 | 1.6 |
| HOSTAPON T | 4 | 4 | 4 |
| MORWET EFW | 2 | 2 | 2 |
| Carrier Hisil HOA | 9.4 | 9.5 | 9.6 |
| (Carrier Loading, wt % | 58 | 63 | 68) |
| Technical Trifluralin | 54.5 | 59.3 | 63.9 |
| Hisil HOA | 37.6 | 33.1 | 28.6 |
| Absorbed water | 1.9 | 1.6 | 1.5 |
| HOSTAPON T | 4 | 4 | 4 |
| MORWET EFW | 2 | 2 | 2 |
| Carrier SIPERNAT 50S | 9.7 | 9.8 | 9.9 |
| (Carrier Loading, wt % | 61 | 66 | 72) |
| Technical Trifluralin | 57.1 | 61.9 | 67.7 |
| SIPERNAT 50S | 34.3 | 29.8 | 24.6 |
| Adsorbed water | 2.6 | 2.2 | 1.7 |
| HOSTAPON T | 4 | 4 | 4 |
| MORWET EFW | 2 | 2 | 2 | b. Method of Preparation:

A series of powders was prepared as per Example 2 with the exception that the carrier loading level was varied and three carriers were used.

Performance Evaluation:

| Carrier Hisil 257 | 9.1 | 92 | 9.3 |
|---|---|---|---|
| Carrier Loading, wt % | 55 | 60 | 66 |
| Short-term Orange Stability | pass | pass | pass |
| Short-term Size Stability | pass | pass | fail |
| Long-term Stability | pass | pass | fail |
| Carrier HISIL HOA | 9.4 | 9.5 | 9.6 |
| Carrier Loading, wt % | 58 | 63 | 68 |
| Short-term Orange Stability | pass | pass | pass |
| Short-term Size Stability | pass | pass | pass |
| Long-term Stability | pass | pass | pass |

-continued

| Carrier SIPERNAT 50S | 9.7 | 9.8 | 9.9 |
|---|---|---|---|
| Carrier Loading, wt % | 61 | 66 | 72 |
| Short-term Orange Stability | fail | pass | pass |
| Short-term Size Stability | fail | fail | fail |
| Long-term Stability | fail | fail | fail |

From the above results it can be seen that formulations with particles whose internal surface area was 450 sq.m/g failed long-term storage stability at all trifluralin loadings used. For the others, H151L HOA was stable at all loadings tried while H151L 257 was unstable at the highest loading level. The powders made using carriers H151L 257 and H151L HOA fall within the preferred ranges of the invention in the case of the powders loaded to within 80 and 87% of the maximum loading (described in Example 15).

Example 105

This example demonstrates the influence (both positive and negative) of various additives to the Reference Formulation described in Example 2.
Materials and Composition:

1. KAOLIN RF, the trade name for an aluminium silicate 99% less than 53 μm, manufactured by Commercial Minerals, Australia.
2. Mica, a potassium aluminium silicate manufactured by Commercial Minerals, Australia, supplied by Commercial Minerals, Australia.
3: Sodium Chloride, AR grade.
4: Calcium Chloride, AR grade.
5: Benzoic Acid, AR grade.
6: Urea, AR grade.
7: DS1850, the trade name for an adjuvant comprising urea complex of polyoxyethylene alkyl ether manufactured by ICI, Australia, supplied by ICI, Australia.
8: VANSIL W30, the trade name for a calcium metasilicate powder manufactured by R. T. Vanderbilt, Connecticut, USA.
9: CLAYFLO KAOLIN, the trade name for a hydrated aluminium silicate 98% <20 microns manufactured by Commercial Minerals, Australia, supplied by Commercial Minerals, Australia.

Composition of the powders designated 10.1 to 10.9 corresponding to additives 1–9 according to the list above:

| Technical trifluralin, (97% pure) | 51.9 wt % |
|---|---|
| HISIL 257 silica | 32.9 |
| Adsorbed water | 1.7 |
| HOSTAPON T dispersant | 3.7 |
| MORWET EFW wetter | 1.8 |
| Additive 1–9 as above | 8.0 | b. Method of Preparation:

To 46 g of Reference Formulation in a 1 liter metal tin was added 4 g of the additive of interest (previously ground, if necessary, and sieved to −106 μm).

The lid was secured and the tin shaken vigorously by hand for 60 seconds to blend. The samples were then temperature cycled in the usual way.

c. Performance Evaluation:

In the table below, samples 10.1 to 10.9 are Reference Formulation plus 8% additive as listed in the components list above, sample 10.10 is Reference Formulation only.

| | 10.1 | 10.2 | 10.3 | 10.4 | 10.5 |
|---|---|---|---|---|---|
| Short-term Orange Stability | pass | pass | pass | fail | pass |
| Short-term Size Stability | pass | pass | pass | fail | fail |
| Long-term Stability | pass | pass | pass | fail | fail |

| | 10.6 | 10.7 | 10.8 | 10.9 | 10.10 |
|---|---|---|---|---|---|
| Short-term Orange Stability | pass | pass | pass | pass | pass |
| Short-term Size Stability | fail | pass | pass | pass | pass |
| Long-term Stability | fail | pass | pass | pass | pass |

Example 11

This example demonstrates that HOSTAPON T, a taurine type dispersion agent, leads to water dispersible trifluralin formulations with good dispersion characteristics.

HOSTAPON T was compared with the dispersers Morwet D 425, Borresperse NA and Polyfon H in the presence of a fixed amount of wetting agent, MORWET EFW.

a. Materials:
1: HOSTAPON T, a sodium-N-methyl-N-oleotaurate manufactured by Hoechst.
2: MORWET EFW, the trade name for a sulphated alky carboxylate and sulphonated alkyl naphthalene sodium salt manufactured by Witco, Dallas, USA.
3: MORWET D 425, the trade name for a sodium naphthalene formaldehyde condensate manufactured by Whitco, Dallas, USA.
4: POLYFON H, the trade name for a sulphonated lignosulphonate sodium salt manufactured by Westvaco, USA.
5: BORRESPERSE NA, the trade name for a sulphonated lignosulphonate sodium salt manufactured by Borregaard, Sarpsborg, Norway, supplied by International Sales and Marketing, Australia.

b. Method of Preparation:

Trifluralin powder was prepared as per Example 3 and hammer milled in the absence of any wetters or dispersers. The wetters and dispersers of interest were added to 5 g of the powder in a 50 ml container and shaken vigorously for 60 seconds to combine. For single components, 6 wt % was used. For two components, the wetter was added at a level of 2 wt % and the disperser at a level of 4 wt %. For three components, all were added at a level of 2 wt %. 2 g of this mixture was then poured into 98 ml of water under rapid magnetic stirring and the wetting time noted. The dispersion was stirred for 2 minutes and then poured into a 100 ml test tube. The samples were allowed to settle for 18 hours and were then completely resuspended by multiple inversions of the stoppered test tube. The samples were then visually inspected for the presence of flocculated aggregates. Good formulations were characterised by the absence of flocs.

| Wetter/Disperser | Wetting Time (seconds) | Flocs Present? |
|---|---|---|
| Hostapon T | 25 | No |
| MORWET EFW | 10 | Yes |
| EFW + Hostapon T | 5 | No |
| EFW + MORWET D 425 | 8 | Yes |
| EFW + BORRESPERSE NA | 5 | Yes |
| EFW + POLYFON H | 6 | Yes |

-continued

| Wetter/Disperser | Wetting Time (seconds) | Flocs Present? |
|---|---|---|
| EFW + Hostapon T + MORWET D 425 | 10 | No |
| EFW + Hostapon T + BORRESPERSE NA | 7 | No |

It is clear from these results that the presence of Hostapon T improved the dispersion characteristics of the Reference Formulation.

Example 12

This example demonstrates that slow cooling during manufacture causes undesirable storage properties. Hot powder after manufacture was slowly cooled in such a manner that it reached 28° C. after 12 hours and then cooled to ambient temperature ("slow cooling"). The powder was compared with powder gradually cooled in such a manner that it reached 22° C. after 6 hours ("normal cooling").

a. Materials and Composition:

The materials and composition of the powders used in this formulation were as per Example 2.

b. Method of Preparation:

The method of preparation was as per Example 2 with the exception that the cooling regime was suitably modified.

| | Normal Cooling | Slow Cooling |
|---|---|---|
| Short-term Orange Stability | pass | fail |
| Short-term Size Stability | pass | fail |
| Long-term Stability | pass | fail |

Slow cooling caused failure of the short-term orange stability test due to high levels of amorphous particles. This led to failure in the short-term size stability test and subsequently in the long-term stability test.

Example 13

This example demonstrates that the formulations of the present invention have equivalent or better bioactivity when compared to a commercially available trifluralin formulation formulated as an emulsifiable concentrate.

a. Materials and Composition:

Commercial trifluralin emulsifiable concentrate (EC) (400 g/L trifluralin) was manufactured by Nufarm, Australia and supplied by Nufarm, Australia. All other materials were as previously described. The powder designated 13.1 was Reference Formulation and the powder designated 13.2 was Reference Formulation +8 wt % kaolin RF.

b. Method of Preparation:

The powders were manufactured as per Example 2. The method of evaluation of the herbicidal activity is described above.

c. Results:

The results (% emergence of weeds as a function of rate of application of herbicide) for a typical glasshouse trial are plotted in FIGS. 1 and 2, and tabled below. From the Figures it can be seen that the formulations of this invention displayed at least equal herbicidal activity when compared to the commercial formulation.

| Rate (g/ha) | 0 | 40 | 80 | 120 | 160 | 240 | 320 | 400 |
|---|---|---|---|---|---|---|---|---|
| Immediate Incorporation Into Soil (FIG. 1): | | | | | | | | |
| EC | 84 | 88 | 50 | 15 | 10 | 0 | 0 | 0 |
| 13.1 | 84 | 80 | 50 | 18 | 6 | 0 | 0 | 0 |
| 13.2 | 84 | 80 | 52 | 14 | 11 | 0 | 0 | 0 |
| 48 Hour Delayed Incorporation Into Soil (FIG. 2): | | | | | | | | |
| EC | 84 | 86 | 78 | 62 | 55 | 38 | 11 | 5 |
| 13.1 | 84 | 82 | 76 | 70 | 24 | 12 | 5 | 4 |
| 13.2 | 84 | 78 | 78 | 55 | 45 | 20 | 5 | 4 |

A summary of the herbicidal activity may be expressed in terms of the rate of herbicide (g/ha) required to reduce the emergence of weeds to 50% (ED50). This result is tabled below for several determinations:

| | Incorporation: Immediate | Incorporation: 48 hours |
|---|---|---|
| EC | 60 | 121 |
| 13.1 | 76 | 105 |
| 13.2 | 76 | 92 |
| EC | 103 | 193 |
| 13.1 | 62 | 98 |
| 13.2 | 72 | 92 |
| EC | 81 | 175 |
| 13.1 | 81 | 135 |
| 13.2 | 81 | 135 |

No significant difference in ED50 was found at immediate incorporation between the various formulations. At delayed incorporation (48 hours), the formulations of this invention (13.1 and 13.2) were somewhat more efficacious (lower ED50) than the commercially available emulsifiable concentrate (EC).

Example 14

This example illustrates the use of Differential Scanning Calorimetry (DSC) in establishing whether trifluralin in a formulation is in the orange or yellow polymorphic form (amorphous may be established by microscopy).

a. Materials and Method:

Sample Preparation:

Reference trifluralin of purity >99.9 wt % (purity determined by capillary gas chromatography) was prepared by recrystallisation of technical trifluralin from methanol and thermally treated in an oven at 44° C. for a period of one hour. This step is necessary to ensure that no yellow polymorphic form trifluralin is present. The sample was ground with a mortar and pestle before use. The yellow polymorphic form was prepared by melting the orange form at 55° C. followed by rapid cooling to <0° C. The sample was maintained at <0° C. and used within 6 hours. Preparation for DSC must be rapid and the sample run promptly to avoid partial interconversion between different polymorphic forms before the determination is complete.

Reference orange polymorph trifluralin loaded powder prepared as per Example 2 was used without further processing. For the yellow polymorph, reference orange polymorph powder was heated at 55° C. to melt the trifluralin and then cooled rapidly to <0° C. The observations made above for yellow polymorph reference trifluralin also apply here.

Normal powder samples were run without any further processing.

2: Instrumentation:

The instrument used was a Perkin-Elmer PC series DSC-7. Calibration was performed using a high purity indium standard and a high purity p-nitro toluene standard (note: this material exists in more than one polymorphic form, to ensure purity the sample was thermally treated in an oven at 48° C. for one hour and ground in a mortar and pestle before use). In a typical run, 5–10 mg of sample was weighed into an aluminium pan and sealed. This was placed into the DSC and thermal transitions in the range 20°–60° C. observed by scanning at a rate of 5° C./min.

b. Results:

The DSC results for pure trifluralin are illustrated in FIG. 3 attached. As may be seen from this Figure, the melting point of the yellow form is lower than that of the orange form. This is summarised in the table below.

The DSC results for the reference trifluralin powder are illustrated in FIG. 4. This Figure shows the depression in melting point observed when the trifluralin is loaded into a carrier. The Figure also illustrates the effect of lower trifluralin purity, the reference powder was made using trifluralin of 97% purity. This causes a broadening of the peak and a lowering of the transition energy. This is summarised in the table below.

FIG. 5 illustrates the DSC result for a sample containing mixed polymorphs. This was prepared by mixing a small amount of orange polymorph powder (ie reference powder) into specially prepared yellow reference powder and quickly running the DSC.

| Sample | Peak (Celsius) | Onset (Celsius) |
| --- | --- | --- |
| Trifluralin (orange) | 49.3 | 47.8 |
| Trifluralin (yellow) | 45.8 | 43.6 |
| Powder (orange) | 44.9 | 38.3 |
| Powder (yellow) | 37.8 | 31.6 |
| Powder (mixed) | 38.1 | 30.6 |

Notes:
1. The onset corresponds to the normal melting point.
2. Reference powder made using 97% pure trifluralin.
3. The temperature results for the mixed polymorph sample are for the yellow polymorph peak.

Example 15

This example describes a method by which the maximum trifluralin loading capacity of a porous carrier may be determined.

a. Materials:

The materials used are as per previous Examples.

b. Method:

A series of powder samples (each containing 3 g of unloaded carrier powder) were heated at 105° C. in an open glass container for 2 hours. Various amounts of molten trifluralin (at 80° C.) were added to the hot carrier powders under stirring for two minutes. The samples were left to cool and crystallise at 15°–20° C. for 24 hours. Crystallisation into the orange form was encouraged by seeding the samples with a small amount of Reference Formulation after one hour of cooling. Each sample was brushed through a 250 μm sieve and the tamped density measured. This was graphed against percentage trifluralin loading. The curve of density vs trifluralin loading is linear in two regions-one below and one above the point of maximum loading. The point of extrapolated intersection of these two lines was noted. This point of intersection was taken to be the maximum trifluralin loading for the carrier.

c. Results:

The above procedure is illustrated in FIG. 6 for the three carrier powders introduced in Example 9. The experimentally determined maximum loading levels from FIG. 6 were used to calculate the loading levels required in all of the examples.

Example 16

This example illustrates the preparation and evaluation of a range of formulations in which a variety of chemically and physically different carriers were used, and in which the wt % loading of trifluralin in the carrier powder was varied in the range 87, 90 and 95% of the experimentally determined maximum loading level (method described in Example 15).

a. Materials and Composition:

The materials used in these formulations were as per Example 2. In addition, three new carriers, FILTERCEL ZEOLEX 7-A and HUBERSORB 600 were used.

1. FILTERCEL, the trade name for a diatomaceous earth (comprising predominantly natural silica with small amounts of aluminium and iron oxide and traces of other oxides) derived from the skeletal remains of single cell aquatic plants known as diatoms of surface area <50 sq.m/g manufactured by Manville, USA, supplied by Filchem, Australia. The particles of this material have a heterogeneous structure reflecting the wide variety of diatom species from which the material is derived.

2. ZEOLEX 7-A, the trade name for a synthetic precipitated sodium aluminosilicate of surface area 115 sq.m/g manufactured by J. M. Huber Corp., USA, supplied by Abel, Lemon and Bleakely, Melbourne, Australia.

3. HUBERSORB 600, the trade name for a synthetic precipitated calcium silicate of surface area 300 sq.m/g manufactured by J. M. Huber Corp., USA, supplied by Abel, Lemon and Bleakely, Melbourne, Australia.

The powder compositions (wt %) are tabled below (powders 16.1, 16.2 and 16.3 correspond to FILTERCEL loaded to 80, 87 and 95% of maximum loading; powders 16.4, 16.5 and 16.6 correspond to ZEOLEX loaded to 80, 87 and 95 % of maximum loading; powders 16.7, 16.8 and 16.9 correspond to HUBERSORB 600, the trade name for loaded to 80, 87 and 95% of maximum loading).

| Carrier Filtercel | 16.1 | 16.2 | 16.3 |
| --- | --- | --- | --- |
| (Carrier Loading (wt %) | 42 | 45 | 49) |
| Technical Trifluralin | 39.4 | 42.3 | 46.0 |
| FILTERCEL | 54.4 | 51.5 | 47.9 |
| Adsorbed water | 0.2 | 0.2 | 0.1 |
| HOSTAPON T | 2 | 2 | 2 |
| MORWET EFW | 4 | 4 | 4 |

| Carrier ZEOLEX 7-A | 16.4 | 16.5 | 16.6 |
| --- | --- | --- | --- |
| (Carrier Loading (wt %) | 42 | 46 | 50) |
| Technical Trifluralin | 38.7 | 42.3 | 46.1 |
| ZEOLEX 7-A | 49.5 | 46.2 | 42.8 |
| Adsorbed water | 3.3 | 3.1 | 2.8 |
| Water of Hydration | 2.7 | 2.6 | 2.5 |
| HOSTAPON T | 1.9 | 1.9 | 1.9 |
| MORWET EFW | 3.9 | 3.9 | 3.9 |

| Carrier Hubersorb 600 | 16.7 | 16.8 | 16.9 |
| --- | --- | --- | --- |
| (Carrier Loading (wt %) | 60 | 64 | 70) |
| Technical Trifluralin | 56.3 | 60.8 | 66.3 |
| HUBERSORB 600 | 32.3 | 28.2 | 23.4 |

-continued

| | | | |
|---|---|---|---|
| Adsorbed water | 2.5 | 2.2 | 1.8 |
| Water of Hydration | 3.1 | 3.0 | 2.7 |
| Hostapon T | 3.9 | 3.9 | 3.9 |
| MORWET EFW | 1.9 | 1.9 | 1.9 |

Note: ZEOLEX 7-A and HUBERSORB 600 contain chemically bound water in addition to physically adsorbed water. The term "water of hydration" refers to the former, and the term "adsorbed water" refers to the latter.

b. Method of Preparation:

A series of powders were prepared as per Example 2, with the exception that the carrier loading level was varied and the three carriers were used.

| Carrier Filtercel | 16.1 | 16.2 | 16.3 |
|---|---|---|---|
| Short-term orange-stability | pass | pass | pass |
| Short-term size-stability | pass | fail | fail |
| Long-term stability | pass | fail | fail |
| Carrier Zeolex 7-A | 16.4 | 16.5 | 16.6 |
| Short-term orange-stability | fail | fail | pass |
| Short-term size-stability | fail | fail | pass |
| Long-term stability | fail | fail | pass |
| Carrier Hubersorb 600 | 16.7 | 16.8 | 16.9 |
| Short-term orange-stability | fail | pass | pass |
| Short-term size-stability | fail | pass | fail |
| Long-term stability | fail | pass | fail |

From the above example it can be seen that the Filtercel powders performed well at the low loading only. Aggregation of the particles occurred at the two higher loadings. The Zeolex 7-A powders performed well at the high loading. At the lower loadings, a high level of amorphous trifluralin was observed. In the case of HUBERSORB 600, high levels of amorphous trifluralin was observed at the low loading. At the high loading aggregation of particles occurred due to excess trifluralin.

Example 17

This example illustrates the preparation and evaluation of a formulation wherein the rate of cooling employed was more rapid than for the Reference Formulation (Example 2).

a. Materials and Composition:

The materials used in this formulation were as per Example 2. The composition was as per Example 2.

b. Method of Preparation:

The formulation was prepared as per Example 3 with the following exceptions:

after loading of the molten trifluralin, the powder was divided into two samples designated 17.1 and 17.2 and cooled as detailed below:

Sample 17.1 (at 58° C. after made) was cooled in a one liter tin at 18°–21° C. and was observed to have reached 25° C. in the core after three hours of cooling. Crystallisation into the orange polymorphic form was observed to begin after 30 minutes but was not complete until after 5.5 hours of cooling (confirmed by orange colour and absence of amorphous trifluralin by microscopy). The powder was left undisturbed for 24 hours, then MORWET EFW and HOSTAPON T were added and the powder hammermilled in a Raymond Lab mill at 2950 rpm through a screen size of 1.6 and 0.58 mm.

Sample 17.2 (at 58° C. after made) was spread as 5 mm thick layer on a 300×300 mm stainless steel tray and cooled at an ambient temperature of 22° C. in a gentle draught of air. This sample was observed to have cooled to 25° C. after 30 minutes and 23° C. after 60 minutes. Crystallisation into the orange polymorphic form was observed to begin after 15 minutes of cooling and was complete after 90 minutes (confirmed by orange colour and absence of amorphous trifluralin by microscopy). After two hours MORWET EFW and HOSTAPON T were added and the powder hammer-milled in a Raymond Lab mill at 2950 rpm through a screen size of 1.6 and 0.58 mm.

c. Performance Evaluation:

| | 17.1 | 17.2 |
|---|---|---|
| Short-term orange-stability | pass | pass |
| Short-term size-stability | pass | pass |
| Long-term size-stability | pass | pass |

From these results it may be seen that rapid cooling to an ambient temperature of 22° C. was not detrimental to product performance. This is in contrast to rapid cooling to an ambient temperature of 5° C. (see Example 4) which resulted in formation of the yellow polymorphic form.

We claim:

1. A solid, water-dispersible, storage-stable trifluralin formulation, comprising orange-stable trifluralin supported inside porous, finely divided, size-stable carrier particles.

2. A formulation according to claim 1, wherein the trifluralin present in the pores of the carrier particles occupies less than 98% of the pore volume of said carrier particles.

3. A formulation according to claim 1, wherein the trifluralin present in the pores of the carrier particles occupies less than 95% of the pore volume of said carrier particles.

4. A formulation according to claim 1, wherein the trifluralin present in the pores of the carrier particles occupies less than 90% of the pore volume of said carrier particles.

5. A formulation according to claim 1, wherein said trifluralin comprises from 50 to 70 wt % of the formulation.

6. A formulation according to claim 1 wherein said trifluralin comprises from 55 to 65 wt % of the formulation.

7. A formulation according to claim 1, wherein at least 80% of said trifluralin is present in the orange polymorphic form.

8. A formulation according to claim 1 wherein at least 90% of said trifluralin is present in the orange polymorphic form.

9. A formulation according to claim 1 wherein at least 95% of said, trifluralin is present in the orange polymorphic form.

10. A formulation according to claim 1, wherein at most 15% of said trifluralin is present in amorphous polymorphic form.

11. A formulation according to claim 1 wherein at most 5% of said trifluralin is present in amorphous polymorphic form.

12. A formulation according to claim 1 wherein at most 1% of said trifluralin is present in amorphous polymorphic form.

13. A formulation according to claim 1, wherein said trifluralin is of a purity 93 to 99 wt %.

14. A formulation according to claim 1, wherein said trifluralin is of a purity of at least 97 wt %.

15. A formulation according to any of claims 1, further comprising at least one compatible wetting agent and/or dispersant additive.

16. A formulation according to claim 15, wherein said additive is a dispersant and is present in an amount of 2 to 10 wt %.

17. A formulation according to claim 16, wherein said dispersant is the sodium salt of N-methyl-N-oleoyltaurate.

18. A formulation according to claim 15, wherein said additive is a dispersant and is present in an amount of 3 to 6 wt %.

19. A formulation according to claim 15, wherein said additive is a wetting agent and is present in an amount of 0.5 to 5 wt %.

20. A formulation according to claim 19, wherein said wetting agent is sodium alkyl naphthalene sulphonate.

21. A formulation according to claim 15, wherein said additive is a wetting agent and is present in an amount of 1 to 3 wt %.

22. A formulation according to any of claim 1, wherein said carrier particles are finely divided porous inorganic particles having a surface area of at least 60 $m^2/g$.

23. A formulation according to claim 22, wherein said inorganic particles are silica or silicate particles.

24. A formulation according to claim 23, wherein said silica or silicate particles have a surface area of 100 to 300 $m^2/g$.

25. A formulation according to claim 23, wherein said silica or silicate particles have a surface area of 150 to 250 $m^2/g$.

26. A formulation according to claim 23, wherein said silica or silicate particles have an adsorbed water content of 2 to 12 wt % before loading of the trifluralin.

27. A formulation according to claim 23, wherein said silica or silicate particles have an adsorbed water content of 3 to 6 wt % before loading of the trifluralin.

28. A formulation according to claim 1, wherein said carrier particles have a particle size not exceeding 70 μm.

29. A formulation according to claim 1, wherein said carrier particles have a particle size in the range of 5 to 30 μm.

30. A formulation according to claim 1 further comprising at least on other particulate active ingredient.

31. A formulation according to claim 30, wherein said at least on other particulate active ingredient is another herbicide.

32. A formulation according to claim 1 further comprising a pulverized clay.

33. A formulation according to claim 32, wherein said pulverized clay is selected from the group consisting of kaolin and attapulgite.

34. A method for the preparation of a solid, water-dispersible, storage-stable trifluralin formulation comprising orange-stable trifluralin supported inside porous, finely divided, size-stable carrier particles said method comprising the steps of adding molten trifluralin to heated carrier particles, maintaining the mixture at a temperature above the melting point of trifluralin for a period of time sufficient to allow substantially all of the trifluralin to be absorbed by the carrier particles, and then gradually cooling the carrier particles to a temperature in the range of 15° to 25° C. over a time period of ½ to 12 hours.

35. A method according to claim 34, further comprising the step of dividing the cooled carrier particles.

36. A method according to claim 35, wherein said cooled carrier particles are divided by hammer milling.

37. A method according to claim 34, wherein the carrier particles are cooled to a temperature in the range of 15 to 20° C., over a time period of 1 to 6 hours.

38. A method for treating soil to prevent emergence of weeds thereon, which comprises:

forming an aqueous dispersion of a water-dispersible trifluralin formulation comprising orange-stable trifluralin supported inside porous, finely divided, size-stable carrier particles; and applying a herbicidally effective amount of said aqueous dispersion to the soil.

* * * * *